US00PP36423P2

(12) United States Plant Patent
Berry

(10) Patent No.: US PP36,423 P2
(45) Date of Patent: Feb. 4, 2025

(54) ***PHOTINIA* PLANT NAMED 'JBN 17001'**

(50) Latin Name: ***Photinia* x *fraseri***
Varietal Denomination: JBN 17001

(71) Applicant: Capstone Plants, Inc., Grand Saline, TX (US)

(72) Inventor: James Berry, Emory, TX (US)

(73) Assignee: Capstone Plants Inc., Grand Saline, TX (US)

( * ) Notice: Subject to any disclaimer, the term of this patent is extended or adjusted under 35 U.S.C. 154(b) by 0 days.

(21) Appl. No.: 18/435,451

(22) Filed: Feb. 7, 2024

(51) Int. Cl.
*A01H 5/00* (2018.01)
*A01H 6/74* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Weatherly IP Solutions, LLC; James M. Weatherly

(57) ABSTRACT

A new cultivar of *Photinia* plant named 'JBN 17001' that is characterized by a naturally branching upright vase-shaped plant habit which achieves a height of 60 cm and a width (at full height) of 30 cm after one year of growth in a 2-gallon container, and a mature height in the landscape of 5 m and a width at full height of 4 m. The mature foliage of 'JBN 17001' is mid green in color. The new foliage growth of 'JBN 17001' is copper in color. The flowers of 'JBN 17001' are very numerous, small and white in color and borne in compound corymbs profusely and continuously in early and mid-spring and then sporadically during summer.

2 Drawing Sheets

Genus and species: *Photinia* x *fraseri.*
Variety denomination: 'JBN 17001'.

BACKGROUND OF THE NEW PLANT

The present invention relates to a new and distinct cultivar of *Photinia*, commonly known as Red Tip *Photinia*, which is grown in USDA hardiness zones 8 and higher as an evergreen ornamental plant for use in the garden and landscape. The new cultivar is known botanically as *Photinia* x *fraseri* and will be referred to hereinafter by the cultivar name 'JBN 17001'.

Whereas cultivars of *Photinia* x *fraseri* in commerce typically bear green foliage with red-colored new season's growth, the new season's foliage of 'JBN 17001' is copper-colored. In addition, whereas it is common for the species and varieties of *Photinia* to exhibit a leaf spot disease, *entomosporium maculatum*, no incidence of this serious and disfiguring disease has been observed on plants of 'JBN 17001' at any time of year. 'JBN 17001' was selected by the inventor for its combination of unique color of new foliage, for its disease resistance and for its dense well-branched plant habit. These characteristics recommend 'JBN 17001' as a hedging plant and as an attractive shrub for the landscape and garden.

'JBN 17001' was selected by the inventor in 2017 as a seedling plant growing amongst many naturally occurring chance seedlings at the inventor's nursery in Grand Saline Texas. These seedlings, including 'JBN 17001' had resulted from the open pollination and self-seedling of plants of the species *Photinia* x *fraseri*. The parents of 'JBN 17001' are unnamed and not released.

The inventor asexually reproduced 'JBN 17001' in 2018 by the method of softwood cuttings in Grand Saline, Texas. Since that time, the unique characteristics of the new *Photinia* plant have been uniform, stable and reproduced true to type in successive generations of asexual reproduction.

SUMMARY

The following traits have been repeatedly observed and represent the characteristics of the new *Photinia* cultivar 'JBN 17001'. 'JBN 17001' has not been tested under all possible conditions and phenotypic differences may be observed with variations in environmental, climatic and cultural conditions, however, without any variance in genotype.

1. 'JBN 17001' exhibits a naturally branching upright vase-shaped plant habit.
2. After one year of growth in a 2-gallon container, plants of 'JBN 17001' achieve a height of 60 cm and a width (at full height) of 30 cm.
3. A mature plant of 'JBN 17001' which is growing in-ground achieves a height of 5 m and a width at full height of 4 m.
4. The previous seasons' foliage of 'JBN 17001' is mid green in color.
5. The current season's new foliage growth of 'JBN 17001' is copper in color.
6. The flowers of 'JBN 17001' are very numerous, small and white in color and borne in compound corymbs.
7. 'JBN 17001' flowers profusely and continuously in early and mid-spring and then sporadically during summer.
8. 'JBN 17001' is resistant to leaf spot disease *entomosporium maculatum.*
9. 'JBN 17001' grows well in moist well-drained soils in full sun to partial shade.
10. 'JBN 17001' is hardy at least to USDA Zone 8.

BRIEF DESCRIPTION OF THE PHOTOGRAPHS

The accompanying color photographs illustrate the overall appearance of the new *Photinia* variety 'JBN 17001' showing colors as true as it is reasonably possible to obtain in colored reproductions of this type. Colors in the photographs may differ from the color values cited in the detailed botanical description, which accurately describe the actual colors of the new variety 'JBN 17001'.

Figure 1:
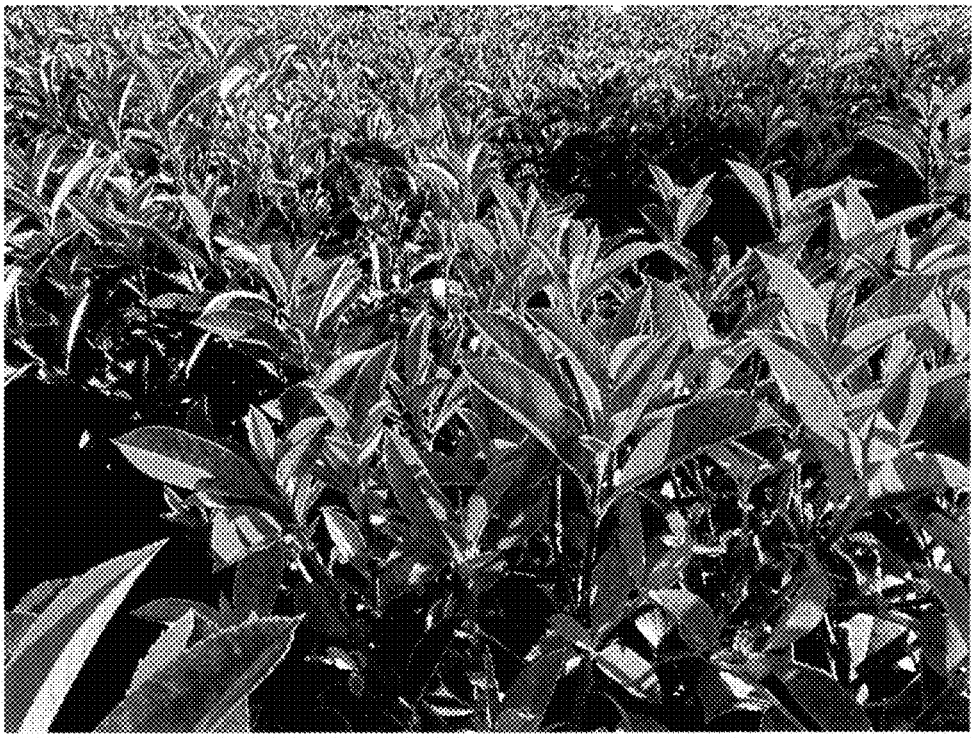
FIG. 1 depicts a crop of plant of 'JBN 17001' growing out of doors in Grand Saline, Texas.
Figure 2:
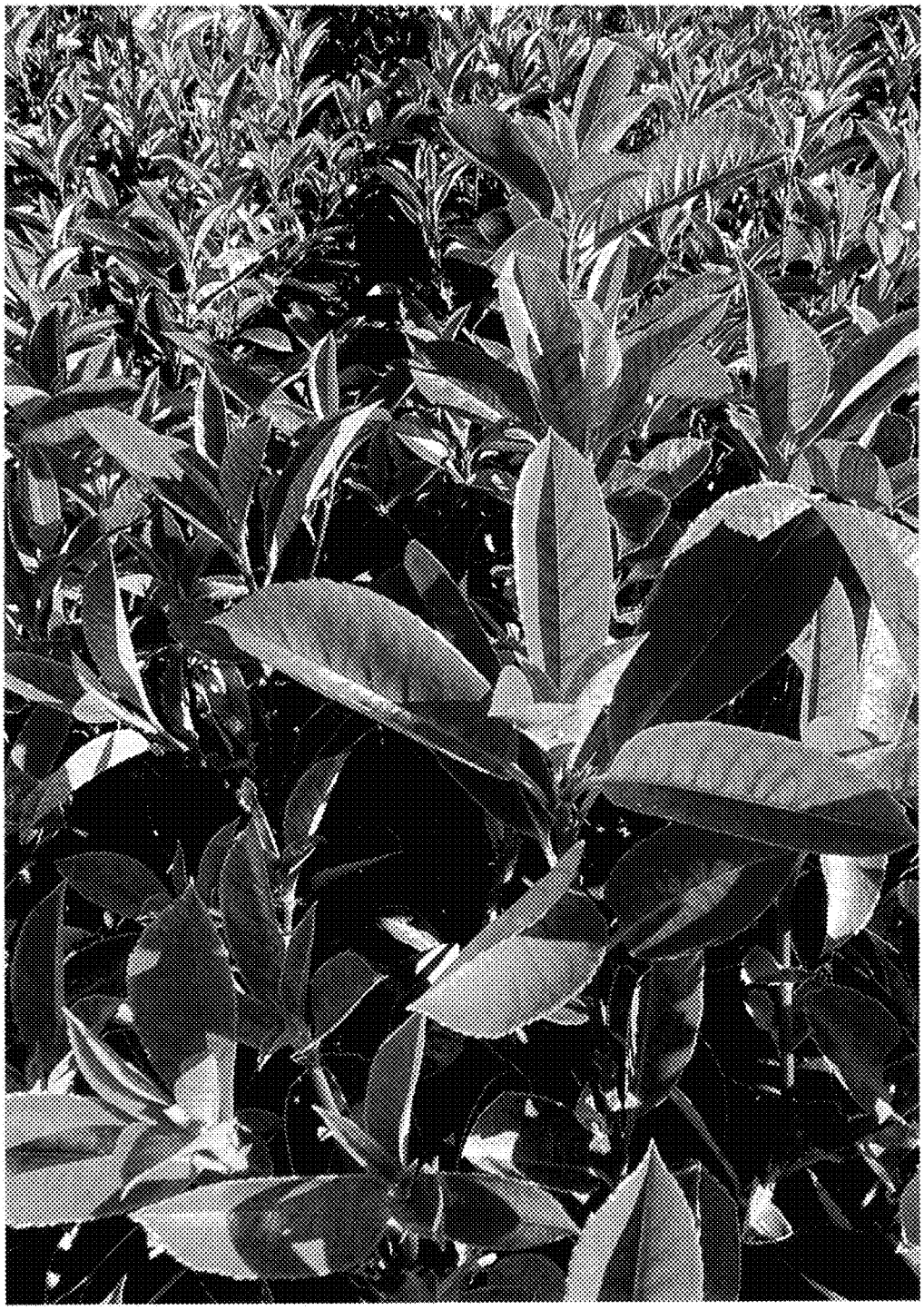
FIG. 2 depicts a close-up views of the newly emerging young foliage of 'JBN 17001'.

Photographs were taken in September 2022 in Grand Saline, Texas from three year old plants which were growing outdoors in 3-gallon containers. No chemicals were used to treat the plants. All photographs were made using conventional techniques and although colors may appear different from actual colors due to light reflectance they are as accurate as possible by conventional photography.

BOTANICAL DESCRIPTION OF THE PLANT

The following is a detailed description of the new cultivar 'JBN 17001'. Data was collected from three-year old plants grown in 3-gallon containers in August 2023 in Grand Saline, Texas. The color determinations are in accordance with the 2007 edition of The Colour Chart of The Royal Horticultural Society, London, England, except where general color terms of ordinary dictionary significance are used. No chemicals were used to treat the plants. Growing conditions are typical of other *Photinia*.

Botanical classification: *Photinia*.

*Variety*.—'JBN 17001'.

*Species*.—x *fraseri*.

*Family*.—Rosaceae.

Parentage: 'JBN 17001' was discovered as a chance seedling amongst a crop of the species *Photinia* x *fraseri*. The identities of the parents are unknown.

Plant description:

*Growth habit*.—Upright, narrow vase shaped.

*Use*.—In containers, as a hedging plant, and in the landscape.

*Suitable container sizes*.—2-gallon to 3-gallon.

*Dimensions in second year (the observed plants) in a 3 gallon container*.—90 cm to 120 cm in height, and 45 cm to 60 cm. in width measured at full plant height.

*Dimensions when mature and planted in-ground*.—5 m in height and 4 m in width measured at full plant height.

*Hardiness*.—At least hardy to USDA Zone 8.

*Propagation*.—Stem cuttings.

*Time to initiate roots*.—10 to 12 weeks are required to produce roots on an initial cutting.

*Crop time*.—One year to 18 months are required to produce a finished two-gallon container from a rooted cutting.

*Root system*.—Fibrous.

*Light*.—Plant in full sun or partial shade.

*Soil*.—Plant in moist but well drained soil.

*Type*.—Deciduous shrub.

*Seasonal interest*.—Colorful copper-colored new foliage growth throughout the season. Numerous small white flowers in spring.

Basal stem (below first pinching or stropping):

*Shape*.—Terete.

*Dimensions*.—16 cm in length, 16 mm in diameter at soil level.

*Color*.—198A.

*Surface*.—Rough, glabrous, no lenticels.

*Color*.—197A.

Branches:

*Branching arrangement*.—Lateral stems arise from base and basal stem after pinching or stopping.

*Branch stem dimensions*.—60 cm to 90 cm in length, 5 mm to 8 mm in diameter.

*Shape*.—Terete.

*Internode distance*.—4 mm.

*Stem color (new growth)*.—Mainly 144B, occasional shades of 181A.

*Stem color (mid-summer)*.—177B.

Foliage:

*General*.—Newly emerging and current season foliage is narrowly elliptical and copper colored. Current season foliage becomes mid-green in the fall and overwinters mid-green becoming broadly elliptical to obovate in its second and subsequent years.

*Leaf arrangement*.—Alternate.

*Leaf division*.—Simple.

*Leaf shape*.—Elliptic to obovate, adaxially concave.

*Leaf attachment*.—Petiolate.

*Petiole shape, cross-section*.—Long, narrow; cylindrical, occasionally elliptical.

*Petiole dimensions*.—17 mm in length and 1 mm in width.

*Petiole color (current season growth)*.—183C.

*Petiole color (previous seasons' growth)*.—137D with anthocyanin coloration 183C towards stem node.

*Leaf dimensions (current season growth)*.—10 cm in length, 43 mm in width.

*Leaf surface (current season growth, adaxial)*.—Glabrous.

*Leaf surface (current season growth, abaxial)*.—Slightly rough to the touch, glabrous.

*Leaf texture*.—Leathery.

*Leaf color (current season growth, adaxial surface)*.—183C.

*Leaf color (current season growth, abaxial surface)*.—185C.

*Leaf apex*.—Acute

*Leaf base*.—Obtuse.

*Leaf margin*.—Minutely serrate.

*Margin serrations*.—Approximately 65 teeth on each margin. Teeth 2 mm in length.

*Leaf venation pattern*.—Pinnate.

*Veins (adaxial surface)*.—Prominent midrib, slightly depressed, color 183C.

*Veins (abaxial surface)*.—Prominent midrib and lateral veins, raised approximately 1 mm, color 187D.

*Leaves (previous seasons' growth)*.—

*Leaf dimensions (previous seasons' growth)*.—10 cm in length, 55 mm in width.

*Leaf surface (previous seasons' growth, adaxial)*.—Glabrous.

*Leaf surface (previous seasons' growth, abaxial)*.—Slightly rough to the touch, glabrous.

*Leaf texture*.—Leathery.

*Leaf color (current season fall growth and previous seasons' growth, adaxial surface)*.—N137D.

*Leaf color* (*current season fall growth and previous seasons' growth, abaxial surface*).—138B.

*Leaf apex*.—Acute

*Leaf base*.—Obtuse.

*Leaf margin* (*previous seasons' growth*).—Minutely serrate.

*Margin serrations*.—Approximately 65 teeth on each margin. Teeth 2 mm in length.

*Leaf venation pattern* (*previous seasons' growth*).—Pinnate.

*Veins* (*previous seasons' growth, adaxial surface*).—Prominent midrib, slightly depressed, color 137D.

*Veins* (*previous seasons' growth, abaxial surface*).—Prominent midrib and lateral veins, raised approximately 1 mm, color 137C.

Inflorescence:

*Inflorescence form*.—Compound corymb present at each leaf axil.

*Inflorescence dimensions*.—35 mm in length

*Quantity of flowers per inflorescence*.—Very numerous, approximately 200.

*Time and duration of flowering*.—Beginning in late April or early May according to climate and season, lasting until July.

Flowers:

*Flower shape, aspect*.—Single, rotate, outward and upward facing

*Length of fully developed inflorescence*.—10 mm-12 mm.

*Height of fully developed inflorescence*.—35 mm.

*Bud*.—Shape: Spherical, apex rounded, base obtuse. Color: White NN155D on emergence, developing light pink blush N155C. Color (flower open): NN155D with light pink blush N155C. Dimensions: 30 mm in length, 10 mm immediately prior to opening. Surface: Smooth, glabrous.

*Peduncle*.—Dimensions: 15 mm to 18 mm in length and 1 mm to 1.5 mm in diameter. Shape: Terete. Color: N34B. Surface: Smooth, glabrous, semi-glossy.

*Pedicels*.—Arrangement: Corymbs of primary branching pedicels along peduncle, secondary branching along primary pedicels. Dimensions: 4 mm to 7 mm in length and 1 mm to 1.5 mm in diameter. Shape: Terete. Color: N34B. Surface: Smooth, glabrous, semi-glossy.

*Calyx, sepals*.—Shape: Funnel-shaped. Calyx dimension: 5 mm in diameter and height. Sepals arrangement: Basally fused and adnate to petals. Sepal quantity: 5 in number, occasionally in semi-fused pairs. Sepal dimensions: 8 mm to 10 mm in length, 2 mm in width. Sepal shape: Lanceolate, basally fused for 3 mm then terminating in unfused triangular apex. Sepal color (both surfaces): 163B. Sepal surface (both surfaces): Lightly pubescent.

*Corolla*.—Shape: Salverform. Dimensions: 30 mm in length, 2 mm in diameter at base, 12 mm in diameter at base of petal lobes. Surface: Glabrous. Tube color (flower freshly opened): Adaxial surface: 49B. Abaxial surface: NN155D. Tube color (flower fully developed, 3-5 days after first opening): Both surfaces: 55A.

*Petals*.—Number: 5, unfused, rotate. Shape: Equal, orbicular, adaxially slightly concave. Apex: Rounded. Base: Truncate. Color (adaxial surfaces): White NN155D with occasional light pink blush N155C. Color (abaxial surface): White NN155D Petal margins 49B towards apex. Surface texture: Smooth, entire.

Reproductive organs:

*Number of stamens*.—20.

*Filament dimensions*.—2 mm in length and less than 0.5 mm in diameter.

*Filament color*.—NN155D.

*Anther shape*.—Ellipsoid, bifid.

*Anther dimensions*.—4 mm in length and 1 mm in width.

*Anther color*.—Initially 161C aging to 164B.

*Pollen color*.—151C.

*Pollen amount*.—Moderate.

*Number of pistils*.—1 or 2 per flower.

*Style*.—Terete, 1.5 mm in length and 0.5 mm in diameter.

*Style color*.—NN155A.

*Style surface*.—Glabrous.

*Stigma shape*.—Capitate, globose.

*Stigma dimensions*.—0.75 mm. in diameter.

*Stigma color*.—NN155A.

*Ovary*.—Not observed.

Fruit:

*Shape*.—Spherical, 5 mm-8 mm. in diameter. Withered sepals remain affixed at apex.

Seed: Not observed.

Susceptibility to diseases: Susceptible to powdery mildew on leaves and stems.

Susceptibility to pests: Susceptible to common horticultural pests including aphids (*aphidoidea*), leaf beetles (*Galerucinae*) and thrips (*thysanoptera*).

Resistance to diseases: Resistant to leaf spot disease *entomosporium maculatum*.

COMPARISON WITH PARENTS AND OTHER KNOWN VARIETIES

In comparison with its parents, the species *Photinia* x *fraseri*, the new foliage growth of 'JBN 17001' is copper in color whereas the parent species *Photinia* x *fraseri* and its cultivars in commerce bears bright crimson red tip new growth on its dark green leaves. The cultivar *Photinia* 'Red Robin' (unpatented) is a widely grown red tipped cultivar of *Photinia*.

'JBN 17001' is resistant to the commonly observed leaf spot disease, *entomosporium maculatum*, which affects the parent species *Photinia* x *fraseri* and many known cultivars of the species *Photinia* x *fraseri*.

I claim:

1. A new and distinct cultivar of *Photinia* plant named 'JBN 17001' as described and illustrated herein.

* * * * *